United States Patent
Manhart (10) Patent No.: US 12,402,850 B2
(45) Date of Patent: Sep. 2, 2025

(54) TRAJECTORY OF A C-ARM OF A C-ARM SYSTEM

(71) Applicant: Siemens Healthineers AG, Forchheim (DE)

(72) Inventor: Michael Manhart, Fürth (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 18/764,624

(22) Filed: Jul. 5, 2024

(65) Prior Publication Data

US 2025/0025118 A1 Jan. 23, 2025

(30) Foreign Application Priority Data

Jul. 19, 2023 (DE) .................... 10 2023 206 853.2

(51) Int. Cl.
*A61B 6/00* (2024.01)

(52) U.S. Cl.
CPC .......... *A61B 6/4441* (2013.01); *A61B 6/5223* (2013.01)

(58) Field of Classification Search
CPC ...... A61B 6/027; A61B 6/4441; A61B 6/5223
See application file for complete search history.

(56) References Cited

U.S. PATENT DOCUMENTS

| | | |
|---|---|---|
| 2002/0090058 A1 | 7/2002 | Yasuda et al. |
| 2008/0089468 A1 | 4/2008 | Heigl et al. |
| 2020/0054297 A1 | 2/2020 | Martinez Ferreira et al. |
| 2022/0031265 A1 * | 2/2022 | Zellerhoff ............. A61B 6/466 |

FOREIGN PATENT DOCUMENTS

| | | |
|---|---|---|
| CN | 101416880 A | 4/2009 |
| DE | 102006041033 A1 | 3/2008 |
| DE | 102012208850 A1 | 4/2013 |
| DE | 102011086754 A1 | 5/2013 |
| DE | 102020209703 A1 | 2/2022 |

* cited by examiner

*Primary Examiner* — Dani Fox
(74) *Attorney, Agent, or Firm* — Lempia Summerfield Katz LLC

(57) ABSTRACT

A method for controlling a C-arm of a C-arm system includes performing a forward leg of a rotation of the C-arm, wherein the forward leg starts at a start position of the forward leg of the C-arm with a lateral offset having a first offset value, and the C-arm is rotated in the forward direction as far as an end position of the forward leg, with the lateral offset being reduced to 0. In addition, a return leg of a rotation of the C-arm is performed, wherein the return leg starts at the end position of the forward leg, and the C-arm is rotated in the return direction as far as an end position of the return leg, with the lateral offset being increased in the opposite direction to the lateral offset of the forward leg up to a second offset value at the end position of the return leg.

14 Claims, 4 Drawing Sheets

TRAJECTORY OF A C-ARM OF A C-ARM SYSTEM

The present patent document claims the benefit of German Patent Application No. 10 2023 206 853.2, filed Jul. 19, 2023, which is hereby incorporated by reference in its entirety.

TECHNICAL FIELD

The disclosure relates to a method for controlling a C-arm of a C-arm system, in which a forward leg of a rotation of the C-arm and a return leg of a rotation of the C-arm are performed. The disclosure also relates to an imaging method for generating three-dimensional (3D) image data of an object under examination, a control facility, and a C-arm system.

BACKGROUND

Modern imaging methods are used to produce two-dimensional or three-dimensional image data that may be used for visualizing an imaged object under examination as well as for other applications.

The imaging methods may be based on detecting X-ray radiation. An X-ray system may include an X-ray source and an X-ray detector opposite from the X-ray source. In the gap between the X-ray source and the X-ray detector, an object under examination (e.g., a patient) is positioned for the imaging from which an image acquisition shall be performed. What are known as C-arm systems are one type of X-ray system. In these X-ray systems, the X-ray source and the X-ray detector, (e.g., a flat-panel detector), are attached to a C-shaped support member, also called a C-arm. By virtue of its shape, the C-arm, along with the associated diagnostic and treatment device or the X-ray detector, may move orbitally about a point of a patient, which point is to be examined or treated, in order to achieve different angular positions between patient and diagnostic or treatment device or X-ray detector without having to reposition the patient.

If a subregion to be examined or treated is meant to be imaged from another position, or if the imaging system or the X-ray detector is meant to be moved as well during imaging of a larger region of the object under examination, then the C-arm may be rotated about a supporting shaft connected to the center of the C-arm.

Three-dimensional (3D) imaging by C-arm angiography devices is now established in the interventional sector. A significant constraint compared with conventional CT systems, however, is the limited imaging area determined by the size of the flat-panel detector. As a result of the limited imaging region, many organs (e.g., lungs, liver) cannot be captured by a single acquisition. In addition, the projection data for almost all regions of the body is cropped or truncated at the sides, leading to image truncation artifacts under standard reconstruction methods.

Solutions employed clinically until now for C-arm 3D imaging with a large imaging region assume that the relative position of the focal point (i.e., the point at which the electrons hit the anode of the X-ray source, or the point from which the X-ray photons of the X-ray radiation are emitted) to the object (patient) being measured is identical. In existing "large volume" protocols on robotic systems, the focal point moves on a circular trajectory around the patient. The distance to the patient therefore remains constant. For angiography systems with a rigid C-arm, this requires that the isocenter of the C-arm is dynamically displaced laterally in both directions in the rotational plane during the rotation about the patient, which only a complex robotic mechanism makes possible.

Figure 1:
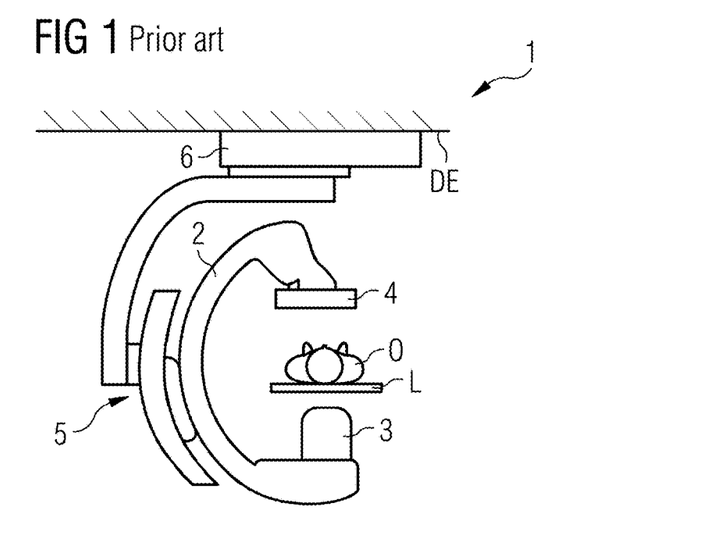
FIG. 1 depicts a schematic representation of a conventional C-arm system.

For traditional isocentric angiography systems, a trajectory with a laterally displaced isocenter is used. In this case, a forward leg and return leg are carried out, and additional one-dimensional lateral movements are performed simultaneously in the rotational plane. This trajectory, which is depicted in FIG. 1, places far fewer demands on the mechanical design of a C-arm system and allows large 3D imaging regions even with C-arm systems of simple construction. Nonetheless, the trajectory shown in FIG. 1 still has practical disadvantages.

For example, the end point of the forward leg does not correspond to the start point of the return leg. Therefore, the system has to be moved between legs. This may result in a time delay of several seconds. The time delay may be kept as short as possible because the patient has to hold their breath during the acquisition.

Additionally, the direction of movement in the lateral direction changes during a leg. In the AP direction (AP is an acronym for "anterior-posterior"), the sign of the velocity in the lateral direction therefore changes. This change may lead to non-reproducible geometrical inaccuracies, in particular in the case of ceiling-suspended systems. Because a 3D reconstruction requires a very high geometrical accuracy of the acquisition, this may lead to image artifacts.

SUMMARY AND DESCRIPTION

Therefore, it is an object of the present disclosure to specify a method and a control facility for controlling a C-arm, which method and control facility may be used to perform the imaging in a time-saving manner and with reduced image artifacts.

This object is achieved by a method for controlling a C-arm of a C-arm system, by an imaging method for generating 3D image data from an object under examination, by a control facility, and by a C-arm system as described herein.

The scope of the present disclosure is defined solely by the appended claims and is not affected to any degree by the statements within this summary. The present embodiments may obviate one or more of the drawbacks or limitations in the related art.

In the method for controlling a C-arm of a C-arm system, (e.g., a ceiling-suspended C-arm system), a forward leg of a rotation of the C-arm is performed, as already mentioned in the introduction. The forward leg is started at a start position of the forward leg of the C-arm with a lateral offset that has a first offset value. A lateral offset may refer to a displacement of the C-arm in the horizontal direction transverse to the patient couch. Thus, the focal point of the X-ray source of the C-arm system is also displaced in a transverse direction. Then, the C-arm is rotated in the forward direction as far as an end position of the forward leg, with the lateral offset being reduced monotonically to a value of 0. The end point of the forward leg has, in addition to the stated value of 0 for the offset, a predetermined value of an orbital angle $\beta$. As will be explained in detail later, the value for the orbital angle of the start point and of the end point is selected such that a sufficiently wide angle range around the object under examination may be covered by imaging. Values of orbital angle $\beta$ of the start points and end points of the forward leg may be at least 90° and −90°, respectively. In certain examples, values of orbital angle $\beta$ of the start points and end points of the forward leg are 100° and −100°, respectively. The values of orbital angle β of the start points and end points of the forward leg may lie in interval ranges of [90°, 120°] and [−90°,−120°], respectively. For mechanical reasons, a ceiling-suspended system may not travel through any desired angulations. It might be possible to shift the start/end angles by up to 20° (e.g., from the value=100°), but, in certain examples, the system cannot mechanically rotate further.

As also mentioned in the introduction, a return leg of a rotation of the C-arm is then performed, i.e., a rotation in a (rotational) direction opposite to the direction of the forward leg. The return leg is started first at the end position of the forward leg, and then the C-arm is rotated in the return direction as far as an end position of the return leg. In the rotation, the lateral offset is monotonically increased in the opposite direction to the lateral offset of the forward leg up to a second offset value at the end position of the return leg. "Increased" is intended in the sense of an increase in magnitude of the lateral offset. For example, if the lateral offset is positive in the forward leg, then the lateral offset in the return leg is negative. If the lateral offset is negative in the forward leg, then the lateral offset in the return leg is positive. The trajectory of the forward leg and of the return leg advantageously are different, so that additional image information may be obtained from a patient in the return leg.

Unlike conventional control methods, in the method disclosed herein, the end point of the forward leg corresponds to the start point of the return leg. Advantageously, the C-arm does not need to be moved between the forward leg and the return leg. Because the patient has to hold their breath during the acquisition, a time delay between the forward leg and the return leg is advantageously avoided or kept as short as possible.

It is also achieved advantageously that the direction of movement of the C-arm in the lateral direction is not changed during a leg, so not during the forward leg nor during the return leg.

Such a change in direction of movement during a leg, in particular in the case of ceiling-suspended systems, may lead to non-reproducible geometrical inaccuracies under the conventional procedure. Because a 3D reconstruction requires a very high geometrical accuracy of the acquisition, these inaccuracies may lead to image artifacts. Advantageously, such image artifacts are now avoided because the direction of movement for the lateral movement of the C-arm is maintained within the movement sequence of the forward leg and within the movement sequence of the return leg.

In the imaging method for generating 3D image data from an object under examination, projection data is captured from the object under examination by applying the method for controlling a C-arm of a C-arm system, and 3D image data is reconstructed on the basis of the captured projection data. The imaging method may be used advantageously to obtain 3D image data from an object under examination, (e.g., a patient), with better quality.

The control facility has a starting unit for controlling a start position of a C-arm in a forward leg of a rotation of the C-arm with a lateral offset that has a first offset value, and for starting the forward leg at the start position of the forward leg, and for starting a return leg of a rotation of the C-arm at an end position of the forward leg.

The control facility also has a rotation unit for rotating the C-arm in the forward leg in the forward direction as far as the end position of the forward leg, with the lateral offset being reduced to a value of 0, and for rotating the C-arm in the return leg in the return direction as far as an end position of the return leg, with the lateral offset being increased in the opposite direction to the lateral offset of the forward leg up to a second offset value at the end position of the return leg. The control facility shares the advantages of the method for controlling a C-arm of a C-arm system.

The C-arm system includes a C-arm, (e.g., a C-curved support member), which may rotate or pivot about a rotational axis or pivot axis. In addition, the C-arm system includes an X-ray source, which is arranged at a first end of the C-arm, (e.g., of the C-curved support member), and an X-ray detector, which is arranged opposite at a second end of the C-arm. The C-arm system also includes the control facility as described herein. The C-arm system shares the advantages of the method for controlling a C-arm of a C-arm system.

Most of the aforementioned components of the control facility and of the C-arm system may be implemented in full or in part in the form of software modules in a processor of a suitable computing system. An implementation largely in software has the advantage that even computing systems already in use may be easily upgraded by a software update in order to work in the manner according to the disclosure. In this respect, the object is also achieved by a corresponding computer program product having a computer program, which may be loaded directly into a computing system, and which contains program segments in order to perform the acts of the method for controlling a C-arm of a C-arm system when the program is executed in the computing system. The computer program product may include in addition to the computer program, if applicable, extra elements such as e.g. documentation and/or extra components, including hardware components, such as e.g. hardware keys (dongles etc.) for using the software.

For transfer to the computing system or to the control facility, and/or for storage on, or in, the computing system or the control facility, a computer-readable medium, for instance a memory stick, a hard disk, or any other portable or permanently installed data storage medium may be used, on which are stored the program segments of the computer program, which program segments may be downloaded and executed by a computing system. For this purpose, the computing system may include one or more interacting microprocessors or the like.

In an embodiment of the method for controlling a C-arm of a C-arm system, the start position of the forward leg of the C-arm has a first angular position. In addition, the end position of the forward leg has a second angular position, and the end position of the return leg has a third angular position. The first angular position and the second angular position and the third angular position may have an angle of the same absolute value. Advantageously, a symmetrical angle range is traveled in the forward leg and the return leg by the C-arm and thus also by the X-ray detector and the X-ray source. Advantageously, a patient, who is lying on a patient couch symmetrically with respect to the anterior-posterior (AP) position, (the patient is exposed to radiation from a vertical direction, the orbital angle equals 0°), may be imaged from each side from the same angle in terms of absolute value.

At least an arc of angle 200° is traveled in order to acquire enough data for a 3D reconstruction. It makes sense to rotate along an arc of 100° both on the "left" and on the "right" of the AP plane. For mechanical reasons, a ceiling-suspended system in particular cannot travel through any desired angulations. It might be possible to shift the start/end angle by up to 20°, however, the system may not mechanically rotate further.

In certain examples, the first angular position has an angle of 100°, the second angular position has an angle of −100°, and the third angular position has an angle of 100°. Image data from an angle range of 200° may be obtained advantageously, allowing an examination region or object under examination to be imaged from different directions. Advantageously, the image information captured from different directions may be combined into a 3D image of the examination region.

Thus an orbital angle of 100° may be used as the start position of the forward leg, and an orbital angle of −100° may be used as the end position of the forward leg. In addition, an orbital angle of −100° is used as the start position of the return leg, and an orbital angle of 100° is used as the end position of the return leg.

As already mentioned above, at least an angle range of 200° may be traveled for the forward leg and the return leg. Additionally, the angle range traveled may lie in a value range of 180° to 240 degrees, or in a value range of 190° to 210°.

In certain examples, the first offset value and the second offset value may have the same magnitude. Because patients may be symmetrical with respect to the sagittal plane, it makes sense to use an equal offset in both directions.

In a variant of the method for controlling a C-arm of a C-arm system, in the forward leg, the rotation of the C-arm in the forward direction includes: maintaining the first offset value of the lateral offset in the forward leg between the start position and an AP position; gradually reducing the lateral offset to the value of 0 between the AP position and a lateral position; and maintaining the lateral offset of value 0 from the region of the lateral position to the end position of the forward leg.

Advantageously, the first offset value, which is used at the start of the forward leg for the lateral offset, is reduced continuously as far as the lateral position to allow uniform imaging.

Alternatively, it may be the case that the offset in the forward leg is reduced to the value of 0 not already at the lateral position but only once at the end position. A continuous change in the offset as far as the end position is advantageously achieved.

In the return leg, the rotation of the C-arm in the return direction may include: maintaining the lateral offset of value 0 in the region from the end position of the forward leg to the lateral position; during the rotation, gradually increasing the lateral offset in the positive lateral direction between the lateral position and the AP position to an end value, which lateral offset is in the opposite direction compared with the lateral offset of the forward leg; and maintaining the offset between the AP position and the end position of the return leg.

Advantageously, no change in offset takes place in the "right-hand" quadrant, so in the forward leg and in the return leg. This is because a change in offset in the right-hand quadrant would have to be compensated by a movement in the reverse direction in the left-hand direction. If the change in offset happens in both directions during the movement, this has the explained disadvantage of the direction of movement in the lateral direction changing during a leg, as is the case in the conventional trajectory shown in FIG. 2. It is therefore advantageous to set the offset in one direction before the rotation starts, so that the offset is not changed during the rotation in the right-hand quadrant, and in the return leg, the offset is simply left the same until the end.

In a likewise variant of the method for controlling a C-arm of a C-arm system, the maximum value of the lateral offset depends on the detector width. The maximum lateral offset may be chosen such that the image acquisitions, which are acquired from the same angle in the forward leg and the return leg, find a connection. If the same value but with opposite sign is chosen as the maximum lateral offset in the forward leg and in the return leg, then the offset may be at most half so large as the detector width. If the maximum lateral offset is smaller, then a region of overlap results between the image data from the forward leg and the return leg that were acquired at the same orbital angle. Adjacent image acquisitions may advantageously be combined more easily by virtue of the overlap.

In certain examples, the maximum value of the lateral offset depends on the overlap of the X-ray detector in the forward leg and in the return leg. The overlap may assume values from 0 to 1. Here, a value of "0" means that there is no overlap, and a value of "1" means that the images acquired at a C-arm position having the same orbital angle in the forward leg and in the return leg fully overlie each other. A larger overlap allows a "smoother" transition between the image data from the two image volumes of the forward leg and the return leg that were captured from the same orbital angle. The two image volumes may be merged by interpolation on the basis of the redundant image data.

In certain examples, the value of the maximum lateral offset is determined from the product of the detector width and the difference formed from the value 1 and the value of the overlap of the X-ray detector in the forward leg and in the return leg at the same orbital angle.

The value of the maximum lateral offset D is then given by:

$$D = \frac{1}{2} \cdot w \cdot (1 - ol), \qquad (1)$$

where w is the width of the X-ray detector and ol is the overlap between the two image acquisitions at the two apexes, or, in general terms, for an image acquisition at the same orbital angle. As already mentioned, the overlap may be chosen between the values 1 and 0.

The maximum lateral offset D also equals half the distance between the two apexes of the trajectories of the C-arm in the forward leg and the return leg.

In an embodiment of the method for controlling a C-arm of a C-arm system, before the acquisition starts, the C-arm is displaced from the standard 3D start position by the necessary maximum lateral offset lv=−D. In the forward leg between the start angle 100° and the AP position at an orbital angle β of 0°, the lateral offset lv remains lv=−D.

"AP" is an abbreviation for "anterior-posterior" and describes a frontal image acquisition of a patient at a position or orientation or an orbital angle β=0°, where the patient is in a recumbent position and the connecting line between the X-ray source and the X-ray detector is vertically orientated. The AP point may also correspond to the apex of the respective trajectories in the forward leg and the return leg. A start angle or orbital angle of 100° means that the connecting line between the X-ray source and the X-ray detector starts at a rotation beyond a lateral orientation in order to be able to travel through a larger angle range for the C-arm acquisition, and hence to obtain additional spatial information about the examination region to be imaged in the patient. At a start angle of 100°, the examination region to be imaged is acquired obliquely from below in figurative terms.

Between an orbital angle of 0°, (i.e. the AP point), and an orbital angle of −90°, (i.e., a lateral orientation of the connecting line between the X-ray source and the X-ray detector), the lateral offset of the C-arm during the rotation is reduced in the positive lateral direction to a lateral offset lv=0, and in the range of the orbital angle of −90° to the end angle of −100° remains at a lateral offset lv=0. In the return leg, the lateral offset lv remains at the value 0 in the range of an orbital angle from −100° to −90°. Between an orbital angle of −90° and 0°, (i.e., between a lateral orientation and an anterior-posterior orientation), the lateral offset lv is increased in the positive lateral direction to a value of lv=+D during the rotation. Between an orbital angle β of 0° and 100°, the lateral offset lv remains at a value of lv=+D.

For the forward leg, the focal point of the X-ray source of the C-arm may describe the following trajectory $a_1$.

For β>0°:

$$a_1 = \begin{pmatrix} SCD \cdot \sin\beta - D \\ SCD \cdot \cos\beta \end{pmatrix} \quad (2)$$

For −90°<β<0°:

$$a_1 = \begin{pmatrix} SCD \cdot \sin\beta - D \cdot \cos\beta \\ SCD \cdot \cos\beta \end{pmatrix} \quad (3)$$

For β<−90°:

$$a_1 = \begin{pmatrix} SCD \cdot \sin\beta \\ SCD \cdot \cos\beta \end{pmatrix} \quad (4)$$

For the return leg, the focal point of the X-ray source of the C-arm may describe the following trajectory $a_2$.

For β>0°:

$$a_2 = \begin{pmatrix} SCD \cdot \sin\beta + D \\ SCD \cdot \cos\beta \end{pmatrix} \quad (5)$$

For −90°<β<0°:

$$a_2 = \begin{pmatrix} SCD \cdot \sin\beta + D \cdot \cos\beta \\ SCD \cdot \cos\beta \end{pmatrix} \quad (6)$$

For β<−90°:

$$a_2 = \begin{pmatrix} SCD \cdot \sin\beta \\ SCD \cdot \cos\beta \end{pmatrix} \quad (7)$$

The orbital angle β describes the following curve:

$$\beta(t) = 100° - \frac{t}{T} \cdot 200°, \; 0 \le t \le T \quad (8)$$

The value SCD gives the distance between the X-ray source and the center of the C-arm system, i.e., the center in which lies the object under examination, in particular the patient.

A reconstruction of 3D image data may be performed as described in DE 10 2020 209 703 A1 on the basis of the projection data acquired in accordance with a variant of the method using the trajectories $a_1$, $a_2$.

BRIEF DESCRIPTION OF THE DRAWINGS

The disclosure is described again below in greater detail using embodiments and with reference to the accompanying figures, in which.

DETAILED DESCRIPTION

FIG. 1 illustrates a C-arm system 1 according to a first embodiment. The C-arm system 1 includes a C-curved support member 2, also referred to as a C-arm 2 for short. An X-ray source 3 is arranged at one end of the C-arm 2, which is shown in FIG. 1 as the lower end, (i.e., the end furthest away from the ceiling DE of a room), from which ceiling the C-arm system 1 is suspended. Additionally, an X-ray detector 4 is arranged on the other end of the C-arm 2, which is shown in FIG. 1 as the upper end, (i.e., the end nearest the ceiling DE).

Between the X-ray source 3 and the X-ray detector 4, a patient couch L is arranged, on which a patient O under examination is arranged. The C-arm 2 is connected by a C-arm suspension 5 to a base 6, which is fastened to the ceiling DE. During an image acquisition of the patient O, X-rays are emitted by the X-ray source 3 and captured by the X-ray detector 4 of the C-arm system 1. The captured measurement signals, or measurement data obtained therefrom, are used for image reconstruction.

Figure 2:
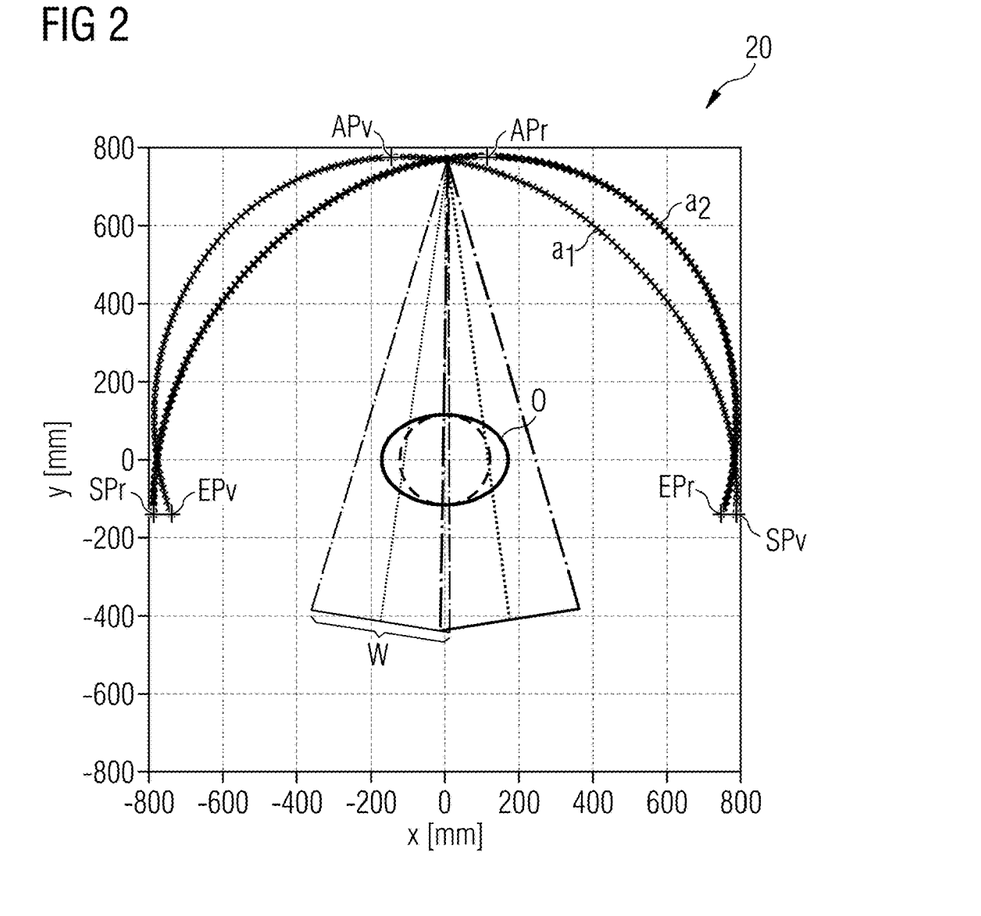
FIG. 2 depicts a schematic representation of a conventional trajectory of a C-arm of a C-arm system.

FIG. 2 shows a schematic representation 20 of a conventional trajectory of a C-arm of a C-arm system. In this case, a forward leg and return leg are performed, and additional one-dimensional lateral movements are performed in the rotational plane. The forward leg starts at the start point $SP_v$ of the forward leg, which is shown in FIG. 2 on the right-hand side of the diagram, at an orbital angle β=100° with a lateral offset lv of −D*cos(100°), where D is the maximum lateral offset. At an orbital angle β=90°, the lateral offset is at lv=0. Up to an orbital angle β of 0°, a lateral offset lv=−D is built up continuously. Then the focus reaches the AP point $AP_v$ of the forward leg, (i.e., the point with the highest y-value), so the apex of the forward leg. Then the lateral offset lv reduces to a value of 0 up to the orbital angle β=−90°. At the end point $EP_v$ of the forward leg, the lateral offset lv again has a value of −D*cos(−100°).

Then, the focal point of the C-arm is shifted to the start point $SP_r$ of the return leg. This focal point lies at an orbital angle β=−100°. The lateral offset lv has a value of +D cos(−100°). At an orbital angle β=−90°, the lateral offset lv has the value 0. Then the lateral offset lv increases to the value of +D up to the orbital angle of 0°. The AP point $AP_r$, (i.e., the apex of the return leg), is then reached. Thereafter, the value of the lateral offset lv reduces to the value 0 up to the orbital angle of 0°, and at the end point $EP_r$ of the return leg has the value D*cos(100°).

The trajectories shown in FIG. 2 place relatively few demands on the mechanical design of the C-arm system 1 and allow large 3D imaging regions even with far less expensive C-arm systems. The end point $EP_v$ of the forward leg does not correspond to the start point $SP_r$ of the return leg. Therefore, the system has to be moved between legs. This may result in a time delay of several seconds. The time delay may be kept as short as possible because the patient O has to hold their breath during the acquisition. The direction of movement in the lateral direction changes during a leg. Therefore, at the AP direction ($\beta=0°$), the sign of the velocity of the offset in the focal point changes in the lateral direction. This change may lead to non-reproducible geometrical inaccuracies, in particular in the case of ceiling-suspended systems. Because a 3D reconstruction requires a very high geometrical accuracy in the capture of the X-ray projection data forming the basis of the 3D reconstruction, this may lead to image artifacts.

For the forward leg, the focal point of the X-ray source of the C-arm describes the following trajectory:

$$a_1 = \begin{pmatrix} SCD \cdot \sin\beta - D \cdot \cos\beta \\ SCD \cdot \cos\beta \end{pmatrix} \quad (8)$$

For the return leg, the focal point of the X-ray source of the C-arm describes the following trajectory:

$$a_2 = \begin{pmatrix} SCD \cdot \sin\beta + D \cdot \cos\beta \\ SCD \cdot \cos\beta \end{pmatrix} \quad (9)$$

The orbital angle describes the following curve:

$$\beta(t) = 100° - \frac{t}{T} \cdot 200°, \, 0 \le t \le T \quad (10)$$

Half the distance D between the two apexes or AP points $AP_v$, $AP_r$, or the maximum offset D, is given by:

$$D = \frac{1}{2} \cdot w \cdot (1 - ol), \quad (11)$$

where w is the width of the X-ray detector and ol is the overlap between the two image acquisitions at the two apexes or AP points $AP_v$, $AP_r$.

Figure 3:
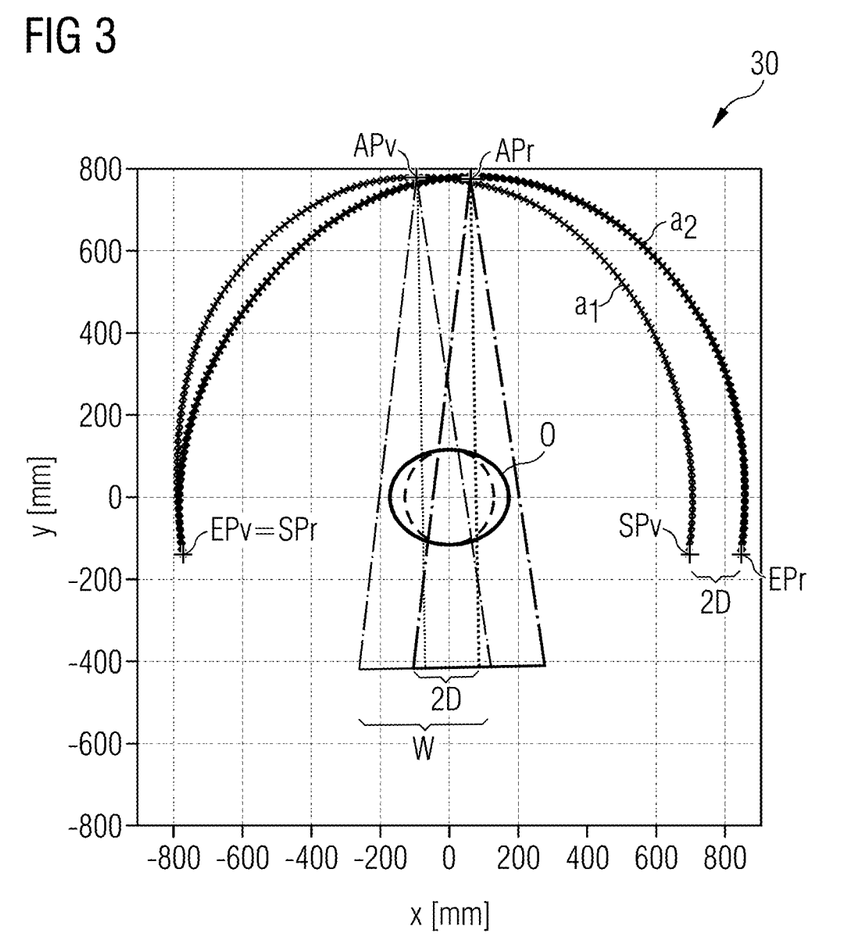
FIG. 3 depicts a schematic representation of a trajectory of a C-arm of a C-arm system according to an embodiment.

FIG. 3 shows a schematic representation 30 of a trajectory of a C-arm of a C-arm system 1 according to an embodiment.

In this case, before the acquisition starts, the C-arm is displaced from the standard 3D start position by the necessary lateral offset lv=−D. In the forward leg between the start angle 100° and an orbital angle of 0°, the lateral offset lv remains at lv=−D. Between an orbital angle $\beta=0°$ and $\beta=-90°$ during the rotation in the forward direction, the offset lv is changed from the value −D to the value lv=0 and remains there in the range of the orbital angle $\beta$ from −90° to the end angle of −100°.

In the return leg, the lateral offset lv=0 is retained in the range of an orbital angle $\beta$ from −100° to −90°. Then, the lateral offset lv increases to a value of +D between the orbital angle $\beta$ of −90° and 0° or the AP position $AP_r$ of the return leg. The lateral offset lv is subsequently kept constant at its maximum value lv=+D as far as an end point $EP_r$ of the return leg.

The trajectories $a_1$, $a_2$ of the forward leg and of the return leg are given by equations (2) to (7), which have been described in detail in the general part of the present patent application.

Figure 4:
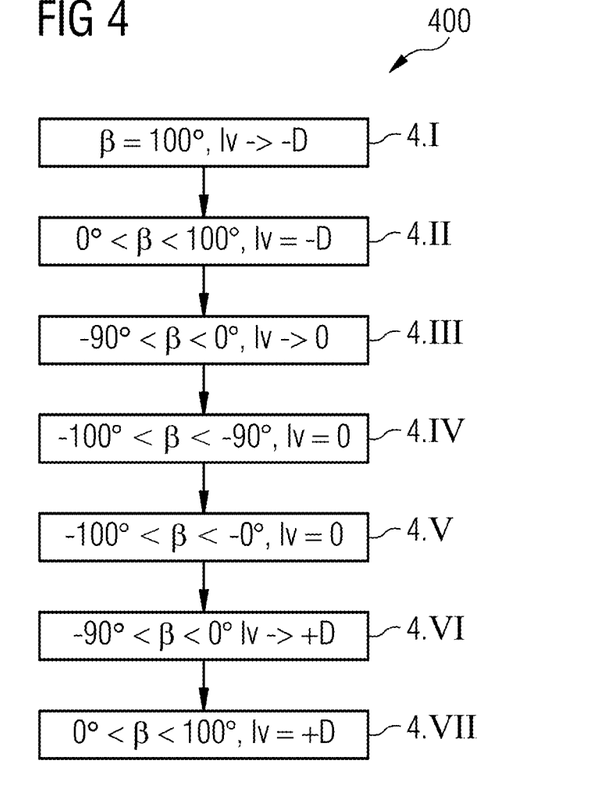
FIG. 4 depicts a flow diagram, which illustrates an example of a method for controlling a C-arm of a C-arm system.

FIG. 4 shows a flow diagram, which illustrates a method for controlling a C-arm of a C-arm system 1 according to an embodiment.

In act 4.I, before the acquisition starts, the C-arm is displaced from the standard centered 3D start position by a lateral offset lv=−D.

In act 4.II, the lateral offset lv=−D is maintained in the forward leg between the start angle 100° and the AP position of 0°.

In act 4.III, during the rotation between the orbital angles $\beta$ of 0° and −90°, the lateral offset lv is gradually reduced in the positive lateral direction to a value of 0.

In act 4.IV, the lateral offset lv=0 is maintained in the range of an orbital angle $\beta$ from −90° to the end angle of −100°.

In act 4.V, the lateral offset of 0 is likewise maintained in the return leg in the range of an orbital angle $\beta$ from −100° to −90°.

In act 4.VI, during the rotation between an orbital angle $\beta$ from −90° and 0°, the lateral offset lv is gradually increased in the positive lateral direction to a value of +D.

In act 4.VII, the lateral offset lv is maintained at the maximum offset lv=+D up to the orbital angle $\beta=100°$, i.e., as far as the end point $EP_r$ of the return leg.

Figure 5:
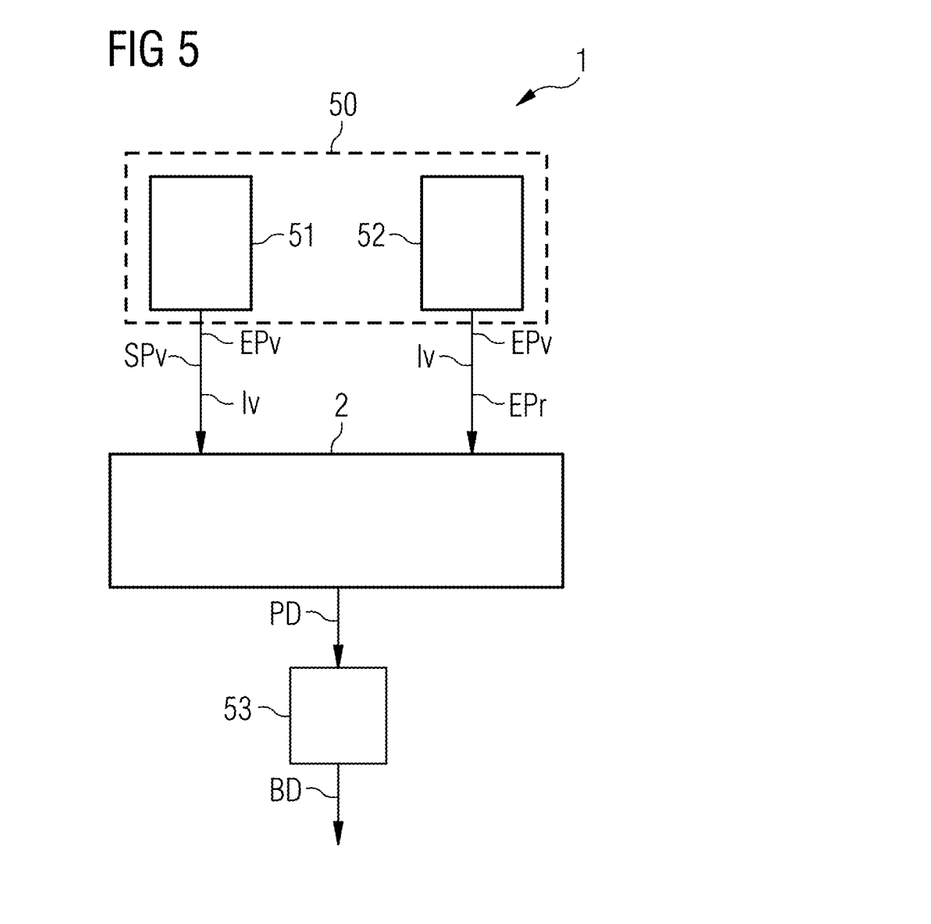
FIG. 5 depicts a schematic representation of a control facility according to an embodiment.

FIG. 5 shows a schematic diagram of a C-arm system 1 having a control facility 50 (shown dashed) according to an embodiment. The C-arm system 1 also includes, in addition to the control facility, a C-arm having an X-ray source and an X-ray detector (not shown).

The control facility 50 has a starting unit 51 for controlling a start position $SP_v$ of a C-arm 2 in a forward leg of a rotation of the C-arm 2 with a lateral offset lv that has a first offset value −D, and for starting the forward leg at the start position $SP_v$ of the forward leg. The starting unit 51 is also configured to start a return leg of a rotation of the C-arm 2 at an end position $EP_v$ of the forward leg, which also constitutes the start position $SP_r$ of the return leg.

The control facility 50 also includes a rotation unit 52 for rotating the C-arm 2 in the forward leg in the forward direction as far as the end position $EP_v$ of the forward leg, with the lateral offset lv being reduced to a value of 0.

The rotation unit 52 is also configured to rotate the C-arm 2 in the return leg in the return direction as far as an end position $EP_r$ of the return leg, with the lateral offset lv being increased in the opposite direction to the lateral offset lv of the forward leg up to a second offset value +D at the end position $EP_r$ of the return leg.

During a forward leg and a return leg, an X-ray detector (not shown), which is arranged on the C-arm 2, acquires projection data PD from an object under examination (not shown).

Part of the C-arm system 1 is also a reconstruction unit 53, which is configured to reconstruct 3D image data BD on the basis of the projection data PD captured from an object under examination by the X-ray detector of the C-arm 2.

Figure 6:
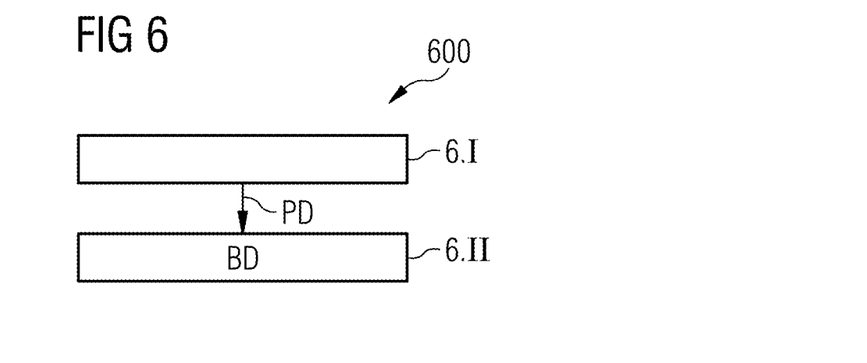
FIG. 6 depicts a flow diagram, which illustrates an imaging method for generating 3D image data from an object under examination according to an embodiment.

FIG. 6 shows a flow diagram 600, which illustrates an imaging method for generating 3D image data BD from an object O under examination according to an embodiment.

In act 6.I, projection data PD is captured from the object O under examination by applying the method for controlling a C-arm 2 of a C-arm system 1.

In act 6.II, 3D image data BD is reconstructed on the basis of the captured projection data PD.

Finally, it shall be reiterated that the described C-arm systems are embodiments, and that the disclosure may be modified by a person skilled in the art without departing from the scope of the disclosure insofar as this is defined by the claims. It is mentioned for the sake of completeness, for example, that the use of the indefinite article "a" or "an" does not rule out the possibility of there also being more than one of the features concerned. Likewise, the term "unit" does not exclude the possibility that the unit includes a plurality of components, which may also be spatially distributed if applicable.

It is to be understood that the elements and features recited in the appended claims may be combined in different ways to produce new claims that likewise fall within the scope of the present disclosure. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for controlling a C-arm of a C-arm system, the method comprising:
   performing a forward leg of a rotation of the C-arm, which includes:
      starting the forward leg at a start position of the forward leg of the C-arm with a lateral offset that has a first offset value; and
      rotating the C-arm in a forward direction as far as an end position of the forward leg, wherein the lateral offset is reduced to a value of 0; and
   performing a return leg of a rotation of the C-arm, which includes:
      starting the return leg at the end position of the forward leg; and
      rotating the C-arm in a return direction as far as an end position of the return leg, wherein the lateral offset is increased in the opposite direction to the lateral offset of the forward leg up to a second offset value at the end position of the return leg.

2. The method of claim 1, wherein the start position of the forward leg of the C-arm has a first angular position,
   wherein the end position of the forward leg has a second angular position,
   wherein the end position of the return leg has a third angular position, and
   wherein the first angular position, the second angular position, and the third angular position have an angle of a same absolute value.

3. The method of claim 2, wherein the first angular position has an angle of 100°,
   wherein the second angular position has an angle of −100°, and
   wherein the third angular position has an angle of 100°.

4. The method of claim 2, wherein the first offset value and the second offset value have a same magnitude.

5. The method of claim 1, wherein the first offset value and the second offset value have a same magnitude.

6. The method of claim 1, wherein, in the forward leg, the rotation of the C-arm in the forward direction comprises:
   maintaining the first offset value of the lateral offset in the forward leg between the start position and an anterior-posterior (AP) position;
   gradually reducing the lateral offset to the value of 0 between the AP position and a lateral position; and
   maintaining the lateral offset of value 0 from a region of the lateral position to the end position of the forward leg.

7. The method of claim 6, wherein, in the return leg, the rotation of the C-arm in the return direction comprises:
   maintaining the lateral offset of value 0 in the region from the end position of the forward leg to the lateral position;
   during the rotation, gradually increasing the lateral offset in a positive lateral direction between the lateral position and the AP position to an end value; and
   maintaining the lateral offset between the AP position and the end position of the return leg.

8. The method of claim 1, wherein, in the return leg, the rotation of the C-arm in the return direction comprises:
   maintaining the lateral offset of value 0 in a region from the end position of the forward leg to a lateral position;
   during the rotation, gradually increasing the lateral offset in a positive lateral direction between the lateral position and an anterior-posterior (AP) position to an end value; and
   maintaining the lateral offset between the AP position and the end position of the return leg.

9. The method of claim 1, wherein a maximum value of the lateral offset depends on a detector width.

10. The method of claim 1, wherein a maximum value of the lateral offset depends on an overlap of an X-ray detector at a same orbital angle in the forward leg and in the return leg.

11. The method of claim 1, wherein a maximum value of the lateral offset is determined based on a product of a detector width and a difference formed from a value of 1 and a value of an overlap of an X-ray detector in the forward leg and in the return leg at a same orbital angle.

12. The method of claim 1, further comprising:
   capturing projection data from an object under examination during the performing of the forward leg of the rotation of the C-arm and the performing of the return leg of the rotation of the C-arm; and
   reconstructing three-dimensional (3D) image data based on the captured projection data.

13. A control facility comprising:
   a starting unit configured to:
      control a start position of a C-arm in a forward leg of a rotation of the C-arm with a lateral offset that has a first offset value;
      start the forward leg at the start position of the forward leg; and
      start a return leg of a rotation of the C-arm at an end position of the forward leg; and a rotation unit configured to:
rotate the C-arm in the forward leg in a forward direction as far as the end position of the forward leg, wherein the lateral offset is reduced to a value of 0; and rotate the C-arm in the return leg in a return direction as far as an end position of the return leg, wherein the lateral offset is increased in the opposite direction to the lateral offset of the forward leg up to a second offset value at the end position of the return leg.

14. A C-arm system comprising:

a C-arm configured to rotate or pivot about a rotational axis or a pivot axis;

an X-ray source arranged at a first end of the C-arm;

an X-ray detector arranged opposite the X-ray source at a second end of the C-arm, wherein the X-ray detector is configured to capture projection data from an object under examination;

a control facility comprising a starting unit and a rotation unit, wherein the starting unit of the control facility is configured to: control a start position of a C-arm in a forward leg of a rotation of the C-arm with a lateral offset that has a first offset value; start the forward leg at the start position of the forward leg; and start a return leg of a rotation of the C-arm at an end position of the forward leg, and wherein the rotation unit of the control facility is configured to: rotate the C-arm in the forward leg in a forward direction as far as the end position of the forward leg, wherein the lateral offset is reduced to a value of 0; and rotate the C-arm in the return leg in a return direction as far as an end position of the return leg, wherein the lateral offset is increased in the opposite direction to the lateral offset of the forward leg up to a second offset value at the end position of the return leg; and a reconstruction unit configured to reconstruct image data based on the captured projection data.

* * * * *